United States Patent [19]
Takei et al.

[11] Patent Number: 5,827,825
[45] Date of Patent: Oct. 27, 1998

[54] SYNTHETIC PEPTIDE, LUNG SURFACTANT CONTAINING THE SAME AND REMEDY FOR RESPIRATORY DISTRESS SYNDROME

[75] Inventors: Tsunetomo Takei; Eiji Ohtsubo; Hirosi Ohkawa, all of Tokyo, Japan

[73] Assignee: Tokyo Tanabe Company Ltd., Tokyo, Japan

[21] Appl. No.: 652,450

[22] PCT Filed: Dec. 7, 1994

[86] PCT No.: PCT/JP94/02057

§ 371 Date: Jun. 5, 1996

§ 102(e) Date: Jun. 5, 1996

[87] PCT Pub. No.: WO95/15980

PCT Pub. Date: Jun. 15, 1995

[30] Foreign Application Priority Data

Dec. 8, 1993 [JP] Japan ................................ 5-307657

[51] Int. Cl.⁶ .................................................. A61K 38/00
[52] U.S. Cl. .......................... 514/12; 514/13; 530/324; 530/325; 530/326; 530/327; 530/328; 530/329
[58] Field of Search ................................. 530/324, 325, 530/326, 327, 328, 329; 514/12, 13

[56] References Cited

FOREIGN PATENT DOCUMENTS

| | | |
|---|---|---|
| 9339056 | 11/1993 | Australia . |
| 368823 | 5/1990 | European Pat. Off. . |
| A-HEI-3- 502095 | 5/1991 | Japan . |
| 88/03170 | 5/1988 | WIPO . |
| 8803170 | 5/1988 | WIPO . |
| 89/04326 | 5/1989 | WIPO . |
| 93/21225 | 10/1993 | WIPO . |

OTHER PUBLICATIONS

Dayhoff, Atlas of Protein Sequence and Structure, vol. 5, p. 96, 1972.
STN Fastnotes.
Richard J. King et al., American Journal of Physiology, No. 223, p. 715, 1972.
Atherton et al., Solid Phase Peptide Synthesis–A Practical Approach, pp. 22–189, Oxford University Press, Oxford, 1989.
Kenichi Akaji et al., Chem. Pharm. Bull., 37 (10), pp. 2661–2664, 1989.

*Primary Examiner*—Cecilia J. Tsang
*Assistant Examiner*—C. Delacroix-Muirheid
*Attorney, Agent, or Firm*—Griffin, Butler, Whisenhunt & Szipl, LLP

[57] ABSTRACT

Synthetic peptides containing the following specific sequence:

Xaa-Pro-Val-Xbb-Xcc-Lys-Arg-W (wherein Xaa is absent or represents Cys or Ser, Xbb represents His or Asn, Xcc represents Leu or Ile and W represents a hydrophobic peptide portion.), an intermediate for producing the peptide, a process for producing the peptide, a lung surfactant comprising the peptide and a lipid mixture and a remedy for respiratory distress syndrome containing the surfactant as the active ingredient. The peptide is easy to isolate and purify and suitable for mass production. As it is highly soluble in methanol and the like, it can readily be blended with a lipid mixture and is suited for the preparation of a lung surfactant. As the lung surfactant has a good supensibility and a potent surface activity, it is useful as a remedy for respiratory distress syndrome.

28 Claims, No Drawings

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Human
        ( F ) TISSUE TYPE: HUMAN LUNG ( x i ) SEQUENCE DESCRIPTION: SEQ ID NO:1:

```
Phe Gly Ile Pro Cys Cys Pro Val His Leu Lys Arg Leu Leu Ile Val
 1               5                  10                      15

Val Val Val Val Val Leu Ile Val Val Val Ile Val Gly Ala Leu Leu
                    20                  25                  30

Met Gly Leu
        35
```

( 2 ) INFORMATION FOR SEQ ID NO:2:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: COW
        ( F ) TISSUE TYPE: BOVINE LUNG ( x i ) SEQUENCE DESCRIPTION: SEQ ID NO:2:

```
Leu Ile Pro Cys Cys Pro Val Asn Ile Lys Arg Leu Leu Ile Val Val
 1               5                  10                  15

Val Val Val Val Leu Leu Val Val Val Ile Val Gly Ala Leu Leu Met
                20                  25                  30

Gly Leu
```

( 2 ) INFORMATION FOR SEQ ID NO:3:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: PIG
        ( F ) TISSUE TYPE: PORCINE LUNG ( x i ) SEQUENCE DESCRIPTION: SEQ ID NO:3:

```
Leu Arg Ile Pro Cys Cys Pro Val Asn Leu Lys Arg Leu Leu Val Val
 1               5                  10                  15

Val Val Val Val Val Leu Val Val Val Val Ile Val Gly Ala Leu Leu
                20                  25                  30

Met Gly Leu
         35
```

( 2 ) INFORMATION FOR SEQ ID NO:4:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x ) PUBLICATION INFORMATION:
        ( A ) AUTHORS: Benson, B J
                  White, R T
        ( B ) TITLE: Human SP-18 and SP-5 derived peptide(s) -
               with alveolar surfactant protein activity, used for treating respiratory distress syndrome,
pneumonia and bronchitis
(C) JOURNAL: Japanese Patent Publication Hei 3-502095
(G) DATE: 16-May-1991

(xi) SEQUENCE DESCRIPTION: SEQ ID NO:4:

Cys Cys Pro Val His Leu Lys Arg Leu Leu Ile Val Val Val Val
1               5                   10                  15
Val Leu Ile Val Val Val Ile Val Gly Ala Leu Leu Met Gly Leu His
            20                  25                  30

(2) INFORMATION FOR SEQ ID NO:5:

(i) SEQUENCE CHARACTERISTICS:
    (A) LENGTH: 35 amino acids
    (B) TYPE: amino acid
    (C) STRANDEDNESS: single
    (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:5:

Phe Gly Ile Pro Cys Cys Pro Val His Leu Lys Arg Leu Leu Leu Leu
1               5                   10                  15
Leu Leu Leu Leu Leu Leu Leu Leu Leu Leu Leu Leu Gly Ala Leu Leu
            20                  25                  30
Met Gly Leu
        35

(2) INFORMATION FOR SEQ ID NO:6:

(i) SEQUENCE CHARACTERISTICS:
    (A) LENGTH: 27 amino acids
    (B) TYPE: amino acid
    (C) STRANDEDNESS: single
    (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:6:

Cys Pro Val His Leu Lys Arg Leu Leu Leu Leu Leu Leu Leu Leu Leu
1               5                   10                  15
Leu Leu Leu Leu Leu Leu Leu Gly Ala Leu Leu
            20                  25

(2) INFORMATION FOR SEQ ID NO:7:

(i) SEQUENCE CHARACTERISTICS:
    (A) LENGTH: 27 amino acids
    (B) TYPE: amino acid
    (C) STRANDEDNESS: single
    (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:7:

Cys Pro Val His Leu Lys Arg Leu Leu Leu Leu Leu Leu Leu Leu Leu

```
        1               5                    1 0                  1 5

Leu   Leu   Leu   Leu   Leu   Leu   Leu   Leu   Leu   Leu   Leu
                        2 0                       2 5
```

( 2 ) INFORMATION FOR SEQ ID NO:8:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:8:

```
    Cys   Pro   Val   His   Leu   Lys   Arg   Leu   Leu   Leu   Leu   Leu   Leu   Leu   Leu
    1                       5                             1 0                         1 5

Leu   Leu   Leu   Leu   Leu   Leu   Leu
                        2 0
```

( 2 ) INFORMATION FOR SEQ ID NO:9:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:9:

```
    Cys   Pro   Val   His   Leu   Lys   Arg   Leu   Leu   Leu   Leu   Leu   Leu   Leu   Leu
    1                       5                             1 0                         1 5

Leu   Leu   Leu
```

( 2 ) INFORMATION FOR SEQ ID NO:10:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:10:

```
    Ser   Pro   Val   His   Leu   Lys   Arg   Leu   Leu   Leu   Leu   Leu   Leu   Leu   Leu
    1                       5                             1 0                         1 5

Leu   Leu   Leu   Leu   Leu   Leu   Leu
                        2 0
```

( 2 ) INFORMATION FOR SEQ ID NO:11:

( i ) SEQUENCE CHARACTERISTICS:
        ( A ) LENGTH: 27 amino acids
        ( B ) TYPE: amino acid
        ( C ) STRANDEDNESS: single (D) TOPOLOGY: linear (ii) MOLECULE TYPE: peptide (iii) HYPOTHETICAL: NO (v) FRAGMENT TYPE: N-terminal (ix) FEATURE:
    (A) NAME/KEY: Modified-site
    (B) LOCATION: 8..23
    (D) OTHER INFORMATION: /product="Norleucine"
        / label= Xaa (xi) SEQUENCE DESCRIPTION: SEQ ID NO:11:

```
Cys Pro Val His Leu Lys Arg Xaa Xaa Xaa Xaa Xaa Xaa Xaa Xaa Xaa
 1               5                  10                  15
Xaa Xaa Xaa Xaa Xaa Xaa Xaa Gly Ala Leu Leu
             20                  25
```

(2) INFORMATION FOR SEQ ID NO:12:

(i) SEQUENCE CHARACTERISTICS:
    (A) LENGTH: 23 amino acids
    (B) TYPE: amino acid
    (C) STRANDEDNESS: single
    (D) TOPOLOGY: linear (ii) MOLECULE TYPE: peptide (iii) HYPOTHETICAL: NO (v) FRAGMENT TYPE: N-terminal (ix) FEATURE:
    (A) NAME/KEY: Modified-site
    (B) LOCATION: 8..23
    (D) OTHER INFORMATION: /product="Norleucine"
        / label= Xaa (xi) SEQUENCE DESCRIPTION: SEQ ID NO:12:

```
Cys Pro Val His Leu Lys Arg Xaa Xaa Xaa Xaa Xaa Xaa Xaa Xaa Xaa
 1               5                  10                  15
Xaa Xaa Xaa Xaa Xaa Xaa Xaa
             20
```

(2) INFORMATION FOR SEQ ID NO:13:

(i) SEQUENCE CHARACTERISTICS:
    (A) LENGTH: 22 amino acids
    (B) TYPE: amino acid
    (C) STRANDEDNESS: single
    (D) TOPOLOGY: linear (ii) MOLECULE TYPE: peptide (iii) HYPOTHETICAL: NO (v) FRAGMENT TYPE: N-terminal (ix) FEATURE:
    (A) NAME/KEY: Modified-site
    (B) LOCATION: 7..22
    (D) OTHER INFORMATION: /product="Norleucine"
        / label= Xaa (xi) SEQUENCE DESCRIPTION: SEQ ID NO:13:

```
Pro Val His Leu Lys Arg Xaa Xaa Xaa Xaa Xaa Xaa Xaa Xaa Xaa Xaa
 1               5                  10                  15
Xaa Xaa Xaa Xaa Xaa Xaa
             20
```

( 2 ) INFORMATION FOR SEQ ID NO:14:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( i x ) FEATURE:
        ( A ) NAME/KEY: Modified-site
        ( B ) LOCATION: 16..23
        ( D ) OTHER INFORMATION: /product="Norleucine"
            / label= Xaa ( x i ) SEQUENCE DESCRIPTION: SEQ ID NO:14:

```
Cys  Pro  Val  His  Leu  Lys  Arg  Leu  Leu  Leu  Leu  Leu  Leu  Leu  Leu  Xaa
1                   5                        10                       15

Xaa  Xaa  Xaa  Xaa  Xaa  Xaa  Xaa
               20
```

( 2 ) INFORMATION FOR SEQ ID NO:15:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:15:

```
Cys  Pro  Val  His  Leu  Lys  Arg  Leu  Leu  Ile  Leu  Leu  Leu  Leu  Leu  Leu
1                   5                        10                       15

Ile  Leu  Leu  Leu  Leu  Ile  Leu
               20
```

( 2 ) INFORMATION FOR SEQ ID NO:16:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( i x ) FEATURE:
        ( A ) NAME/KEY: Modified-site
        ( B ) LOCATION: 14
        ( D ) OTHER INFORMATION: /product="Norvaline"
            / label= Xaa ( i x ) FEATURE:
        ( A ) NAME/KEY: Modified-site
        ( B ) LOCATION: 18
        ( D ) OTHER INFORMATION: /product="Norvaline"
            / label= Xaa ( x i ) SEQUENCE DESCRIPTION: SEQ ID NO:16:

Cys Pro Val His Leu Lys Arg Leu Leu Leu Leu Val Leu Xaa Leu Val
1               5                   10                  15

Leu Xaa Leu Leu Leu Leu Val
        20

(2) INFORMATION FOR SEQ ID NO:17:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:17:

Cys Pro Val His Leu Lys Arg Leu Leu Leu Leu Leu Leu Leu Leu Leu
1               5                   10                  15

Leu Leu Leu Leu Leu Leu Trp
        20

(2) INFORMATION FOR SEQ ID NO:18:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:18:

Cys Pro Val Asn Leu Lys Arg Leu Leu Leu Leu Leu Leu Leu Leu Leu
1               5                   10                  15

Leu Leu Leu Leu Leu Leu Leu
        20

(2) INFORMATION FOR SEQ ID NO:19:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (ix) FEATURE:
        (A) NAME/KEY: Modified-site
        (B) LOCATION: 8..23
        (D) OTHER INFORMATION: /product="Norleucine"
            / label= Xaa (xi) SEQUENCE DESCRIPTION: SEQ ID NO:19:

Cys Pro Val Asn Ile Lys Arg Xaa Xaa Xaa Xaa Xaa Xaa Xaa Xaa Xaa
1               5                   10                  15

Xaa Xaa Xaa Xaa Xaa Xaa Xaa 2 0

(2) INFORMATION FOR SEQ ID NO:20:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:20:

Cys Pro Val His Leu Lys Arg Val Val Val Val Val Val Val Val Val
1               5                       10                      15

Val Val Val Val Val Val Val Gly Ala Leu Leu
                20                  25

(2) INFORMATION FOR SEQ ID NO:21:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:21:

Cys Pro Val His Leu Lys Arg Ile Ile Ile Ile Ile Ile Ile Ile Ile
1               5                       10                      15

Ile Ile Ile Ile Ile Ile Ile Gly Ala Leu Leu
                20                  25

1

SYNTHETIC PEPTIDE, LUNG SURFACTANT CONTAINING THE SAME AND REMEDY FOR RESPIRATORY DISTRESS SYNDROME

BACKGROUND OF THE INVENTION

The present invention relates to a novel synthetic peptide. To be more detailed, it concerns the synthetic peptide which, by being compounded with a lipid mixture, exhibit potent surface activity. The invention also concerns an intermediate for the production of such synthetic peptide, a process for producing such synthetic peptide, a lung surfactant comprising the peptide and a lipid mixture and a lung surfactant remedy for respiratory distress syndrome containing said peptide as the active ingredient.

Respiratory distress syndrome is a disease in which the surface activity of the alveolar surface is lowered due to a lack of lung surfactant. This leads to the collapsing of the alveoli which, in turn, results in severe respiratory disorders. This syndrome occurs frequently among immature neonatants and exhibits a high mortality rate. It is known that lung surfactant compositions are highly effective against neonatal respiratory distress syndrome.

Adults are also afflicted by hypoxemia due to various causes and there are many examples wherein diffuse ground-glass-like shadows are seen in both lungs in chest X-ray photographs and respiration failure occurs despite controlling respiration with a respirator, etc. Ueda and associates (in: Hiromoto Yasuda, "Biosurfactants. Chapter 3. Medical Practices Using Surfactants. Section 1. Clinical Applications of Surfactants. V. Aspiration Pneumonia and Surfactants." p.184, 1990, Science Forum, Co.Ltd.) have reported 2 cases of pneumonia in adults (Ie. the cases of: ① nitrate gas aspiration pneumonia and ② recurrent aspiration pneumonia originating from brain tumor, that caused hypoxemia and lead to the deterioration of the general condition and respiratory failure) in which significant improvements were obtained and lives were saved by the injection of lung surfactant into the respiratory tract. Postoperative respiratory failure may occur after heart operations since respiration is stopped during the operation. The effect of lung surfactants on such respiratory failures has also been reported (Shuichi Nosaka et al, Journal of Japanese Medical Society for Biological Interface, Vol. 22, p. 66, 1991).

The substitution therapy of administering lung surfactants from the exterior and via the respiratory tract therefore shows significant therapeutic effects for respiratory distress syndrome.

Recently, 4 types of apoproteins were found that are unique to the lung surfactants of mammals. These are surfactant apoprotein A and surfactant apoprotein D, which are hydrophilic, and surfactant apoprotein B (shall be referred to hereinafter as SP-B) and surfactant apoprotein C (shall be referred to hereinafter as SP-C), which are hydrophobic (Toyoaki Akino and Yoshio Kuroki, Respiration and Circulation, vol.38, No.18, p.722, 1990; Hiromoto Yasuda et al, Biosurfactants: Chapter 2. The Biochemistry of Surfactants—Surfactants and Apoproteins, p.131, 1990, Science Forum, Co.Ltd.).

The SP-C (sequence No.1) derived from human lungs consists of 35 amino acids and is a highly hydrophobic apoprotein that is rich in valine and has phenylalanine as the N-terminal amino acid. The SP-C's isolated from the lung of bovines (sequence No.2), pigs (sequence No.3), rats, etc. also consist of 34 to 35 amino acids and although the amino acid sequences at the N-terminal differ for different species, they exhibit an extremely high homology with human SP-C.

Japanese patent publication No. Hei-3-502095 also indicates that a synthetic peptide (sequence No.4), with the below mentioned 32 amino acid sequence that is part of the structure of SP-C, is the minimum unit that exhibits high surface activity, that mixtures of this peptide and lipids are effective against respiratory distress syndrome and that comparisons of the surface activities of this minimum unit peptide and that of other synthetic peptide with shorter amino acid sequences show that the loss of surface activity is due not to the loss of a specific amino acid but to the reduction in the length of the peptide chain.

Previously, a part of the present inventors have found that mixtures of a synthetic peptide (shall be referred to hereinafter as TP-C), the structure of which is part of the structure of SP-C, and a lipid are effective in the treatment of respiratory distress syndrome and have applied for a patent on this subject (Japanese patent application No. Hei-5-518188).

With regards to the production of synthetic peptides, it is generally said that, as the amino acid sequence of the peptide becomes long, the formation of defective peptides during production becomes frequent, isolation and purification become difficult, the amount of time required for production becomes large, bulk production becomes difficult, etc.

Also, due to quality maintenance considerations, pulmonary surfactant compositions are frequently provided as a dry powder composition to be administered as a physiological saline suspension upon use. Methods such as adding suspending agents such as mannitol (Japanese patent publication No. Hei-1-60451) and lyophilization at a primary freezing temperature of $-1°$ to $-10°$ C. have been proposed for improving the suspendability of the lung surfactant. However, these methods are complicated in operation and the development of simpler methods of producing agents has been desired.

The lung surfactant composition (referred to hereinafter as S-35), made by compounding SP-C with a lipid mixture comprised of a choline phosphoglyceride, an acid phospholipid and a fatty acid analogue, has an extremely poor dispersability in physiological saline, making it difficult to prepare a suspension that is uniform enough to be used as a composition. The reasons include the forming of disulfide bonds by the cysteine residues in the peptide which make the peptide highly cohesive and the high hydrophobicity of the lung surfactant itself.

Since TP-C has low solubility in general solvents, it was necessary to use trifluoroacetic acid (TFA) to prepare the lung surfactant composition. TP-C thus had problems, as that much concentrating and drying time were required to remove as much TFA as possible and that the lung surfactant suspension became acidfied during the preparation of the lung surfactant composition due to the residual TFA.

The present inventors have studied synthetic peptides diligently in consideration of the above and have arrived at the invention upon finding out that novel synthetic peptides (referred to hereinafter as the "synthetic peptides of the invention"), that contain the below-mentioned amino acid sequence with a hydrophilic peptide part of a specific sequence at the N-terminal and a hydrophobic peptide part comprised mainly of Leu and/or Nle at the C-terminal, are easy to isolate and purify, can be produced in bulk quantities, are well-soluble in formic acid, TFA, trifluoroethanol, dimethylsulfoxide (DMSO), chloroform, chloroform-methanol mixtures, methanol, ethylene chlorohydrin and tetrahydrofuran and, in particular, have a significantly high solubility in methanol in comparison to synthetic SP-C and TP-C. The present inventors have also found out that lung surfactants prepared from the synthetic peptides of the invention and lipid mixtures exhibit, even when produced by ordinary lyophilization methods carried out at −20° C. or below and without the addition of suspending agent, good, uniform suspendability. The compositions of the invention are superior to S-35 or to a synthetic lung surfactant (referred to hereinafter as "SF-3"; Japanese patent publication No. Hei-2-87685) comprised only of a lipid mixture consisting of a choline phosphoglyceride, an acid phospholipid and a fatty acid analogue or to a substance (referred to hereinafter as "S-TA"; Japanese patent publication No. Sho-61-9924) containing, along with a fatty acid, a substance comprised of a phospholipid, a neutral lipid, total cholesterol, carbohydrates and minute amounts of proteins present in the lungs of mammals. Yet the compound of the present invention exhibit a strong surface activity that is equivalent to that of S-35, S-TA or a lung surfactant comprised of TP-C and a lipid mixture.

Xaa-Pro-Val-Xbb-Xcc-Lys-Arg-W　　　　　　　　　I.

(Xaa may not be present or may represent Cys or Ser, Xbb represents His or Asn, Xcc represents Leu or Ile and W represents a hydrophobic part.)

The synthetic peptide of the invention contains a hydrophilic peptide part described by the undermentioned specific sequence at the N-terminal and a peptide part having a hydrophobic peptide part comprised mainly of of Leu and/or Nle at the C-terminal and is a synthetic peptide which exhibits a strong surface activity when compounded with a lipid mixture.

Xaa-Pro-Val-Xbb-Xcc-Lys-Arg　　　　　　　　　II.

(Xaa may not be present or may represent Cys or Ser, Xbb represents His or Asn and Xcc represents Leu or Ile.)

Although the hydrophobic peptide part is comprised of such hydrophobic amino acids as Leu, Nle, Ile, Val, Phe, Nva and Trp, it is mainly comprised of 12 or more and preferably 12–20 Leu and/or Nle of molecules. Although it is preferable in terms of ease of synthesis, etc. that this hydrophobic peptide part be comprised of the same hydrophobic amino acid, it may be comprised of a suitable of sequence of Leu and Nle molecules or may contain 1 to 5 molecules of Ile, Val, Nva, Trp and other hydrophobic amino acids within its sequence.

The synthetic peptides of the invention also include synthetic peptides in which an amino acid or a peptide is added to the N-terminal and/or C-terminal of the above-mentioned synthetic peptide. The amino acid to be added to the N-terminal may be Cys or Ser. Furthermore, a peptide with the sequence, Phe-Gly-Ile-Pro may be added to the N-terminal. The thiol group or the hydroxyl group present in the above-mentioned synthetic peptide may be acylated by a fatty acid with 14 to 18 carbon atoms and preferably by palmitic acid or may be acetoamidomethylate. The peptide to be added to the C-terminal may have the sequence, Gly-Ala-Leu-Leu or Gly-Ala-Leu-Leu-Met-Gly-Leu.

Furthermore, the synthetic peptides of the invention also include synthetic peptides (except for peptides having the partial structure of natural SP-C) which contain a peptide group that exhibits good hydrophilicity and which exhibits strong surface activity when compounded with lipid mixtures even upon addition, removal and substitution of one or a plurality of the comprising amino acids.

The synthetic peptide of the invention may be produced by chemical or genetic engineering methods although chemical methods are preferred in terms of isolation and purification.

Chemical production methods of the synthetic peptide of the invention include stepwise elongation methods and fragment condensation methods involving liquid phase or solid phase synthesis methods such as azide methods, acid chloride methods, acid anhydride methods, mixed acid anhydride methods, DCC methods, activated ester methods (p-nitrophenol ester method, p-hydroxysuccinimide ester method, carboimidazol method, etc.), oxidation-reduction methods and DCC-activation methods.

The invention also provides a fragment condensation method for producing the synthetic peptides of the invention in which a hydrophilic peptide group with a protected N-terminal and protected functional side chains serves as the intermediate for production.

In comparison to the stepwise elongation method, the fragment condensation method provides easier purification of the targeted substance, is more suited to bulk synthesis and has the characteristic that losses due to unexpected errors can be prevented. The synthetic peptides of the invention can be produced by condensing the hydrophobic part with the priorly prepared hydrophilic peptide part with a protected N-terminal and protected functional side chains by a liquid phase or solid phase synthesis method. The protective groups for the N-terminal and the functional side chains are not particularly restricted as long as they are protecting groups that are used in ordinary peptide synthesis. The 9-fluorenylmethyloxycarbonyl (Fmoc), the 2-chlorobenzyloxycarbonyl (2-CLZ) or the t-butyloxycarbonyl (Boc) group may be used as the protective group for the terminal amino acid group; Fmoc, Boc or the carbobenzoxy (Z) or the tosyl (Tos) group may be used as the protective group for Lys; Trt, Fmoc, Boc, Dnp, Bom, Bzl or Tos may be used as the protective group for His; and Mtr, Pmc, Mts or Tos may be used as the protective group for Arg. Thus, the peptides that can be used as the intermediate for the production of the synthetic peptide of the invention include Fmoc-Pro-Val-His(Trt)-Leu-Lys(Boc)-Arg(Mtr), Fmoc-Pro-Val-Asn-Leu-Lys(Boc)-Arg(Mtr) and Fmoc-Pro-Val-Asn-Ile-Lys(Boc)-Arg(Mtr).

The lung surfactant (hereinafter referred to as the "surfactant of the invention") may be produced by compounding a synthetic peptide of the invention with a lipid mixture consisting of a choline phosphoglyceride, an acid phospholipid and a fatty acid analogue.

It is suitable to set the composition ratios so that the weight ratios of each of these components, with respect to the total dry weight of the final product, are 0.1–5.0% (W/W) for the synthetic peptide, 50.6–80.5% (W/W) for the choline phosphoglyceride, 4.5–37.6% (W/W) for the acid phospholipid and 4.6–24.6%(W/W) for the fatty acid analogue.

Examples of choline phosphoglycerides that can be used suitably in the surfactant of the invention include 1,2-diacylglycero-(3)-phosphocholines such as 1,2-dipalmitoylglycero-(3)-phosphocholine (dipalmitoylphosphatidylcholine), 1,2-distearoylglycero-(3)-phosphocholine, 1-palmitoyl-2-stearoylglycero-(3)-phosphocholine and 1-stearoyl-2-palmitoylglycero-(3)-phosphocholine, etc.; 1-alkyl-2-acylglycero-(3)-phosphocholines such as 1-hexadecyl-2-palmitoylglycero-(3)-phosphocholine and 1-octadecyl-2-palmitoylglycero-(3)-phosphocholine, etc.; and 1,2-dialkylglycero-(3)-phosphocholines such as 1,2-dihexadecylglycero-(3)-phosphocholine, etc. Although optical isomers based on the second carbon of the glycerol residue exist for the above compounds, any of the D-, L- and DL-forms can be used for the surfactant of the invention. Besides the single choline phosphoglyceride compounds mentioned above, mixtures comprised of two or more different 1,2-diacylglycero-(3)-phosphocholines with acyl groups, preferably two saturated acyl groups, with 12 to 24 carbon atoms or mixtures of such mixtures and the abovementioned single compounds may be used as the choline phosphoglyceride.

Examples of suitable acid phospholipids include 1,2-diacyl-sn-glycero-(3)-phosphoric acid (L-α-phoshphatidic acid), 1,2-diacyl-sn-glycero-(3)-phospho-L-serine (phosphatidylserine), 1,2-diacyl-sn-glycero-(3)-phospho-sn-glycerol (phosphatidylglycerol) and 1,2-diacyl-sn-glycero-(3)-phospho-(1)-L-myo-inositol (phosphatidylinositol). The first and second positions of these compounds may be substituted by the same acyl group or by different acyl groups. Here, it is preferable for the acyl group to have 12 to 24 carbon atoms.

Examples of suitable fatty acid analogues include free fatty acids, alkali metal salts of fatty acids, fatty acid alkyl esters, fatty acid glycerine esters and fatty amides and mixtures comprised of two or more of the above and fatty alcohols and fatty amines.

In the present specification, "fatty acid analogues" include the above-mentioned fatty alcohols and aliphatic amines.

Myrisitic acid, palmitic acid or stearic acid can be used as the free fatty acid although palmitic acid is preferred.

The sodium salts, potassium salts, magnesium salts and calcium salts of the above-mentioned free fatty acids can be used as the alkali metal salt of a fatty acid although sodium palmitate is preferred. Lower alkyl esters with 1 to 4 carbon atoms can be used as the fatty acid alkyl ester although ethyl palmitate is preferred. Monoglycerine esters can be used as the fatty acid glycerine ester although monopalmitin is preferred.

Alcohols with 14 to 18 carbon atoms may be used as the fatty alcohol although hexadecyl alcohol is preferred. Amines with 14 to 18 carbon atoms may be used as the aliphatic amine although hexadecyl amine is preferred.

The above-mentioned choline phosphoglyceride, acid phospholipid and fatty acid analogue may be products isolated from plants or animals, semi-synthetic products or synthetic chemical products and commercially available products of such may be used.

The surfactant of the invention may be produced by drying and solidifying under reduced pressure, a mixture of solutions of the peptide of the invention and the above-mentioned lipid mixture and suspending the residue thus obtained in a suitable suspending liquid and then lyophilization.

Examples of solvents that may be used to prepare the solution of the peptide of the invention include, formic acid, TFA, trifluoroethanol, DMSO, chloroform-methanol, chloroform, methanol, ethylene chlorohydrin and tetrahydrofuran.

Examples of solvents that may be used for the preparation of the lipid mixture solution include chloroform and chloroform-methanol [1:2–5:1 (V/V)].

Examples of the suspending liquid include water and water-ethanol mixtures [4:1–20:1 (V/V)] although water-ethanol mixtures are preferred. The suspending operation is performed for 5–60 minutes and preferably for 15–30 minutes at 30°–60° C. and preferably at 40°–50° C.

The surfactant of the invention prepared by this method unavoidably contains a small amount of residual water. However, it is preferable for the surfactant to be dried until the weight ratio of the residual water is 5.0% (W/W) or less with respect to the total weight. If the surfactant is dried to this level, the ethanol residue will become undetectable in cases where water-ethanol mixtures are used.

Dry powder compositions of the surfactant of the invention may be suspended and dispersed uniformly in a solution with a suitable physiological concentration of a univalent or divalent metal salt, for example 0.9% sodium chloride or 1.5 mM calcium chloride, or a physiological buffer solution containing such salts by using a shake-hand or variable-speed mixer or an ultrasonic generation device.

The surface activity, suspendability and pharmacological properties of the surfactant of the invention thus produced shall now be described.

(1) Surface activity (a) Surface tension lowering effect

The surface tension lowering effects were measured according to the method by Tanaka et al (Journal of Japanese Medical Society for Biological Interface, vol.13, No.2, p.87, 1982).

A suspension of the surfactant of the invention was dropped onto physiological saline (with a surface area of 54.0 $cm^2$) so that there was 1.0–2.0 μg of the surfactant of the invention per 1 $cm^2$. The said surface area was compressed and expanded in the range 54.0–21.6 $cm^2$ in 2 to 5 minutes and the surface tension was measured continuously at 37° C. with a Wilhelmy's surface balance (made by Kyowa Interface Science Co.Ltd.). The maximum surface tensions were 24.7–34.1 dyne/cm and the minimum surface tensions were 0.2–8.7 dyne/cm, indicating that the surface tension lowering effects of the surfactants of the invention lower the surface tension of physiological saline.

Measurements by the same method of the surface tension lowering effect of SF-3 resulted in maximum surface tensions of 26.8–50.3 dyne/cm and minimum surface tensions of 1.0–13.5 dyne/cm.

The surface tension of physiological saline itself at 37° C. was 70.5 dyne/cm.

(b) Spreadability over a gas-liquid interface

A suspension of the surfactant of the invention was dropped onto the surface of physiological saline so that there was 0.8–1.5 μg of the surfactant per 1 $cm^2$ of the physiological saline surface and the variation in time of the surface tension was measured by the vertical plate method from the point immediately after the suspension was dropped. The measurement temperature was 37° C.

The equilibration refers to the time it takes for the surface tension to reach a fixed value from the point immediately after the sample was dropped and the value after such a time is called the equilibrium surface tension.

The surfactants of the invention formed a film at the gas-liquid interface in a short time of 30–60 seconds and lowered the surface tension to 26.7–34.3 dyne/cm.

Measurements by the same method of the gas-liquid interface spread effect of SF-3 showed that the surface tension was 38.1–52.9 dyne/cm after 120 seconds.

This indicates that the surfactant of the invention spread quickly to the gas-liquid interface and lowers the surface tension rapidly.

(c) Adsorbability to a gas-liquid interface

Physiological saline suspensions containing 0.2–1.0 mg of the surfactant of the invention per 1 ml at 37° C. were prepared and the rate of adsorption of the suspended surfactants of the invention to the gas-liquid interface of physiological saline were measured.

The adsorbability were measured according to the method by King et al (American Journal of Physiology, No.223, p.715, 1972).

That is, the suspension was injected to the bottom of a 5 cm diameter teflon tank containing physiological saline which was then stirred with a magnetic stirrer. The absorbability was determined from the variation of the surface tension after the stirring was stopped.

The surfactant of the invention lowered the surface tension to between 28.3 and 36.8 dyne/cm in 30 to 100 seconds after the stirring was stopped and the surface tension remained constant thereafter.

This indicates that the surfactants of the invention, in the suspended condition, floated and adsorbed to the gas-liquid interface in 30 to 100 seconds and formed a film with strong surface activity.

When measured in the same manner, SF-3 indicated that constant surface tensions from 42.2 to 58.3 dyne/cm were attained in 150 seconds or more.

This indicates that the gas-liquid interface adsorption effect of SF-3 is lower than that of the surfactants of the invention and that the surfactant of the invention have a strong ability to promote surface adsorption.

(2) Suspendability

Suspendability tests of the lung surfactant were carried out in accordance with the method indicated in Japanese utility model publication No. Hei-4-76965.

That is, the suspendability was evaluated from the dispersion efficiencies at specific times after starting the suspending operation and from the maximum dispersed particle size 2 minutes after starting the suspending operation.

Dispersion efficiency tests were performed as follows. 60 mg each of the lung surfactants were dispensed into 20 ml vials. 2 ml of physiological saline was then added to each of the said vials and the vials were placed on a Iwaki KM Shaker-V-S type shaker (made by Iwaki Sangyo Co.Ltd.) and shaken at a rate of 270 strokes/min. The dispersion conditions of each sample were visually observed with a magnifying glass every 30 seconds during the first 2 minutes after the shaking was started, every 1 minute between 2 minutes and 4 minutes after the shaking was started and every 10 minutes after 4 minutes after the shaking was started.

The suspension conditions were evaluated at each specified time by 2 persons with each person evaluating 10 samples each. The samples were judged to be suspended if there were no small masses within the container and if the composition was dispersed uniformly in the physiological saline to form a white, consistent suspension.

The dispersion efficiencies were determined by each person at each specified time as the percentages of the samples for which suspension was completed with respect to the total number (10 vials) of samples and were indicated as the averages of the values determined by the two persons.

The maximum dispersed particle sizes were measured as follows: 60 mg each of the lung surfactant was dispensed into 20 ml vials. 2 ml of physiological saline was then added to each vial and the vials were shaken continuously for 2 minutes under the same shaking conditions mentioned above. The largest particle in the suspension was then searched for with a microscope and its diameter was determined by measuring with calipers. It was thus found that the surfactants of the invention were mostly suspended within 2 minutes and that their maximum particle sizes were 0.8 mm or less, indicating that their suspendability was good.

(3) Pharmacological properties (a) Acute toxicity

The acute toxicities of the surfactants of the invention were tested using 5-week-old male ICR mice and Wister rats. The oral $LD_{50}$'s and peritoneal $LD_{50}$'s for the mice were 2.4–10.0 g/kg and 1.0–5.0 g/kg, respectively, while those for the rats were 1.5–5.0 g/kg and 1.5–2.5 g/kg, respectively.

(b) Subacute toxicity

The surfactants of the invention were administered intraperitoneally to mature Wister rats at daily doses of 300–600 mg/kg for 1 month. There were no variations in the weight of the rats and no anomalies were seen upon histological observations with the naked eye.

(c) Alveolar volume-maintaining effects

Rabbit immature fetuses produce hardly any lung surfactant at a gestation period of 27 days and are in a lung surfactant deficient condition. They are thus used as model animals for studying neonatal respiratory distress syndrome.

5 rabbit fetuses at a gestation period of 27 days were used and the alveolar space volumes (referred to hereinafter as lung volume) were measured under varied airway pressures at 37° C.

The neck of the fetus was cut and continuous measurements were made with a water manometer attached to the trachea from 5 minutes after administering the surfactant of the invention via the respiratory tract. The airway pressure was raised to 30 cm $H_2O$ with a 2-channel independent-drive syringe pump No. 940 (made by Harvard Co., USA) to expand the alveoli. The airway pressure was then reduced to 0cm $H_2O$ to collapse the alveoli while measuring the lung volumes at various $H_2O$ pressures. The lung volumes were then indicated as milliliters per 1 kg weight (ml/kg).

The surfactants of the invention (60 mg/kg) were administered by directly injecting 0.05–0.5 ml of physiological saline suspensions with surfactant concentrations of 1.0–6.0% (W/V) into the respiratory tract.

The lung volume at the point when the pressure was reduced to 5 cm $H_2O$ indicates the functional residual capacity and the larger this volume, the higher the activity of the lung surfactant.

As a control, physiological saline was administered instead of the surfactant of the invention. The lung volumes (at 5 cm $H_2O$) of the rabbit immature fetuses of the control group were 1–5 ml/kg, indicating that the alveoli were hardly expanded.

Full term fetuses at a gestation period of 30 days have normal levels of lung surfactant. Their lung volumes (at 5 cm $H_2O$) are 35–53 ml/kg, indicating that the alveoli are adequately expanded and that normal respiration can be carried out.

In cases where SF-3 was administered, the lung volumes (at 5 cm $H_2O$) of the immature fetuses were 15–25 ml/kg, indicating inadequate expansion of the alveoli.

When the surfactants of the invention were administered, the lung volumes (at 5 cm $H_2O$) were 39–55 ml/kg, indicating that the surfactants of the invention improve the lung volume of immature fetuses to normal levels.

As described above, the synthetic peptides of the invention possess the effect of strongly enhancing the surface activity of lipid mixtures. It is thus possible to prepare therapeutic agents for respiratory distress syndrome, which are effective in terms of surface activity, suspendability and pharmacological properties, from surfactants of the invention comprised of the synthetic peptides of the invention and a lipid mixture.

Compositions having the surfactant of the invention as the active ingredient can also be used in the treatment of other diseases for which lung surfactants show a therapeutic effect, including, postoperative respiratory failure, asthma, bronchitis, neonatal necrotis enteritis, gastric and duodenal ulcers, respiratory diseases caused by viruses and tubal obstruction and in the prevention of oviduct adhesion and postoperative organ adhesion and as expectorants.

Therapeutic agents for respiratory distress syndrome provided by the invention contain 50–1000 mg of the surfactant of the invention per dose for use in children and 500–5000 mg of the surfactant per dose for use in adults. Such doses are prepared by suspending in water, physiological saline or buffers, etc., that can be tolerated physiologically, at concentrations of 1.0–10.0% (W/V). These are then used by administering within 72 hours after the occurrence of the respiratory disorder by injecting or nebulizing into the respiratory tract 1 to 10 times. The compositions may also be inspired as it is, in other words as a powder agent and without suspending. The dosage, method of use and frequency may be changed suitably according to the symptoms of the patient and concurrent treatment.

The therapeutic agent of the invention may contain, as needed, such pharmaceutic aids as stabilizing agents, preservatives, isotonizing agents, buffering agents, suspending agents, anti-oxidation agents and surfactants or such drugs as bronchodilators, antiallergic agents, carcinostatic agents, antiviral agents, anti-inflammatory agents and antifungal agents.

The dosage may suitably take the form of a liquid or a powder. The therapeutic agents of the invention can be filled in sealed containers such as vials and ampules and preserved as sterile compositions.

DESCRIPTION OF THE PREFERRED EMBODIMENTS

The invention shall now be described in more detail with reference to the following examples.
(1) Production of the peptide In the examples described below, the molecular weight of the synthesized peptide was measured with a fast atom bombardment mass spectometory method (FABMS). The mass analyzer used was a JMS-S102A (JEOL.Ltd.) and a cesium gun (10 KeeV) was used for the ion source.

EXAMPLE 1

The peptide (peptide A) indicated by [sequence No.5] was synthesized on a phenylacetoamidomethyl (PAM) resin surface by a solid-phase synthesis method in accordance with the method described in "The Peptides" (Gross E. and Meinenhofe J. eds., Barany G. and Merrifield R. authors, vol. 2, pp.1–284, Academic Press, New York, 1980).

The C-terminal leucine residue was transformed into t-butyloxycarbonyl-leucine (Boc-Leu) and bonded to the PAM resin via an oxymethylphenylacetoamidemethyl bond. After bonding the C-terminal, the Boc-Leu-PAM resin (0.70 mol/g, 0.35 g) was transferred to the reaction container of a peptide synthesizer (Model 990E, Beckman Instruments, Inc.). Amino acids, to which protective treatments were applied, were then added in the N-terminal direction on the surface of the resin by a symmetric anhydride method to synthesize a fully-protected peptide-O-resin. However, in the condensation of arginine, double coupling was performed using N,N-dicyclohexylcarbodiimide/hydroxybenzotriazole [Connie et al, Chem.Ber., 103, 788–798 (1970)].

The N-terminal amino group of all amino acids were protected with the Boc group and the functional side chains were protected with the following groups before using the amino acids in the reaction:

Arg-Tos: (tosyl)
Lys-2CLZ: (2-chlorobenzyloxycarbonyl)
Cys-4MeBzl: (4-methylbenzyl)
His-Tos: (tosyl)

The condensation reactions of these were confirmed with the ninhydrin method Kaiser test. The fully-protected peptide-O-resin (155 mg) was swelled for 5 minutes in dichloromethane. The N-α-Boc protective group was then removed with TFA containing 1% (v/v) indole and 0.1% (v/v) ethanedithiol. Next, the peptide was cleavaged from the resin by treating the unprotected peptide-O-resin with anhydrous hydrogen fluoride (HF) (11 ml), to which p-cresol (1 ml), p-thiocresol (0.2 g) and DMSO (1 ml) were added, for 60 minutes at 0° C.

The HF and DMSO were distilled off under vacuum at 0° C. The removed peptide and the resin were washed three times with cold diethyl ether (15 ml) and the removed peptide was extracted by washing four times in cold TFA (5 ml). The extracted liquid was filtered immediately and ice-cold water (150 ml) was added to precipitate the crude peptide. The crude peptide was then centrifuged at 1000×g and 0° C. for 30 minutes and recovered as precipitate. This precipitate was washed with diethyl ether (15 ml). After repeating this washing process using diethyl ether, ethyl acetate and distilled water, 84 mg of peptide A was obtained.

This crude peptide was dissolved in a 50% aqueous solution of DMSO and was purified by reverse phase high performance liquid chromatography (HPLC) using μ-Bondaspheres and a C8-300 column to collect pure peptide A.

Elution was performed for 5 minutes using a 50% aqueous solution of acetonitrile, containing 0.1% TFA, as the eluant. Elution was then performed for 30 minutes under a linear concentration gradient formed by the abovementioned eluant and 80% aqueous solution of acetonitrile containing 0.1% TFA.

The presence of the peptide in the eluate was monitored at 245 nm (spectrophotometer; Japan Spectroscopic Co.Ltd. Model 870-UV) and with a differential refractometer (Shimadzu Manufacturing corporation Model RID-6A).

FABMS (M+H$^+$); 3837.1 (calculated molecular weight; 3835.9)

EXAMPLE 2

The peptide (peptide B) with [sequence No.6] was synthesized by a solid phase method using the multi-peptide solid phase synthesis system, "Kokku-San" (trade name; Kokusan Chemical works Co.Ltd.), and by referring to the methods indicated in "Solid Phase Peptide Synthesis—A Practical Approach" by E. Atherton and R. C. Sheppard (pp.25–189, Oxford University Press, Oxford) and by Kenichi Akagi et al (Chem. Pharm. Bull., 37(10), pp.2661–2664, 1989).

N-α-9-fluorenylmethyloxycarbonyl-leucine-O-resin (Fmoc-Leu-O-resin) (0.20 mmol/0.5 g), in which N-α-9-fluorenylmethyloxycarbonyl-leucine (Fmoc-Leu) is bonded to a 4-(hydroxymethyl) phenoxymethyl-copolymer (styrene 1% divinyl benzene) resin, was used as the starting resin. This resin was swelled for 20 minutes with N,N-dimethylformamide (DMF) and then washed four times with DMF. 20% piperidine in DMF was then added and the mixture was shaken to remove the protective groups. This operation was repeated three times to remove the protective groups completely. This was followed by washing three times with DMF, three times with N-methyl-2-pyrrolidone and three times with DMF again to remove the excess piperidine in the resin. The presence of piperidine was checked at this time using pH paper.

DMF (6 ml), Fmoc-Leu (0.5 mmol), N-hydroxybenzotriazole (0.5 mmol) and N,N'-diisopropylcarbodiimide (0.5 mmol) were then added and the mixture was shaken for 90 minutes to carry out the condensation reaction. The resin was then washed four times with DMF to eliminate the excess reagents. This condensation reaction was tested with the ninhydrin method kaiser test.

The synthesis plan was followed thus and amino acids were added step by step in the N-terminal direction on the surface of the resin to thereby form a peptide-O-resin with the N-terminal and the functional groups fully protected.

The condensation reactions for the introduction of Arg, Lys, His, Pro and Cys were carried out twice for 120 minutes each.

Thereafter, 20% pyridine in DMF was added to the protected peptide-O-resin to remove the Fmoc protective group of the N-terminal. The peptide-O-resin was then washed six times with DMF and six times with methanol and dried under reduced pressure. m-cresol (0.2 ml), 1,2-ethanedithiol (0.5 ml), thioanisole (1.2 ml), TFA (7.5 ml) and trimethylsilylbromide (1.4 ml) were then added to the dried peptide-O-resin (100 mg) while stirring and cooling with ice. The mixture was then stirred for 120 minutes while cooling with ice to remove the protective groups from the functional side chains and to remove the peptide from the resin and then filtered through a glass filter (G3). The filtrate was concentrated under reduced pressure to approximately 5 ml with an evaporator. Diethyl ether was then added to precipitate the peptide. This peptide precipitate was collected with a glass filter (G3), washed five times with diethyl ether and upon drying under reduced pressure, 60 mg of peptide B was obtained.

The N-terminal amino group of all amino acids were protected with the Fmoc group and the functional side chains were protected with the following groups before using the amino acids in the reaction:

Arg-Mtr: (4-methoxy-2,3,6-trimethylbenzensulfonyl)
Lys-Boc: (t-butyloxycarbonyl)
Cys-Trt: (trityl)
His-Trt: (trityl)

Approximately 100 mg of the crude peptide was dissolved in TFA (1 ml) and four times this amount of mobile phase solvent, ie. 10 mM β-mercaptoethanol in TFA-dichloromethane (5:95, V/V), was added to prepare a 20 mg/ml sample solution for purification by HPLC using an Asahipak GS-510 (φ7.5×500 mm) column (trade name; Asahi Chemical Industry Co.Ltd.) to thereby collect pure peptide B.

10 mM β-mercaptoethanol in TFA-dichloromethane (5:95, V/V) was used as the eluant and elution was carried out at flow rate of 0.8 ml/min for 80 minutes. The presence of the peptide in the eluate was monitored at 245 nm (spectrophotometer; Japan Spectroscopic Co.Ltd. Model 870-UV) and with a differential refractometer (Shimadzu corporation Model RID-6A).

FABMS (M+H$^+$); 3017.9 (calculated molecular weight; 3016.9)

EXAMPLE 3

The peptide (peptide C) with [sequence No.7] was prepared in the same manner as in Example 2.

FABMS (M+H$^+$); 3116.0 (calculated molecular weight; 3115.1)

EXAMPLE 4

The peptide (peptide D) with [sequence No.8] was prepared in the same manner as in Example 2.

FABMS (M+H$^+$); 2663.7 (calculated molecular weight; 2662.5)

EXAMPLE 5

The peptide (peptide E) with [sequence No.9] was prepared in the same manner as in Example 2.

FABMS (M+H$^+$); 2211.2 (calculated molecular weight; 2209.9)

EXAMPLE 6

The peptide (peptide F) with [sequence No.10] was prepared in the same manner as in Example 2.

FABMS (M+H$^+$); 2647.5 (calculated molecular weight; 2646.4)

EXAMPLE 7

The peptide (peptide G) with [sequence No.11] was prepared in the same manner as in Example 2.

FABMS (M+H$^+$); 3018.1 (calculated molecular weight; 3016.9)

EXAMPLE 8

The peptide (peptide H) with [sequence No.12] was synthesized by the solid phase synthesis method using a solid phase multi-peptide synthesis system in the same manner as in Example 2.

N-α-9-fluorenylmethyloxycarbonyl-norleucine-O-resin (Fmoc-Nle-O-resin) (0.20 mmol/0.5 g) resin was used as the starting resin. This resin was swelled for 20 minutes with DMF and then washed four times with DMF. 20% piperidine in DMF was then added and the mixture was shaken to remove the protective groups. This operation was repeated three times to remove the protective groups completely. This was followed by washing nine times with DMF to remove the excess piperidine in the resin. The presence of residual piperidine was checked at this time using pH paper.

DMF (6 ml), Fmoc-Nle (0.5 mmol), N-hydroxybenzotriazole (0.5 mmol) and N,N'-diisopropylcarbodiimide (0.5 mmol) were then added and the mixture was shaken for 90 minutes to carry out the condensation reaction. The resin was then washed four times with DMF to eliminate the excess reagents. This condensation reaction was tested with the ninhydrin method kaiser test.

The synthesis plan was followed thus and amino acids were added step by step in the N-terminal direction on the surface of the resin to thereby form a peptide-O-resin with the N-terminal and the functional groups fully protected.

The condensation reactions for the introduction of Arg, Lys, His, Pro and Cys were carried out twice for 120 minutes each.

Thereafter, 20% pyridine in DMF was added to the protected peptide-O-resin to remove the Fmoc protective group of the N-terminal. The peptide-O-resin was then washed six times with DMF and six times with methanol and dried under reduced pressure. m-cresol (0.2 ml), 1,2-ethanedithiol (0.5 ml), thioanisole (1.2 ml), TFA (7.5 ml) and trimethylsilylbromide (1.4 ml) were then added to the dried peptide-O-resin (100 mg) while stirring and cooling with ice. The mixture was then stirred for 120 minutes while cooling with ice to remove the protective groups from the functional side chains and to remove the peptide from the resin and then filtered through a glass filter (G3). The filtrate was concentrated under reduced pressure to approximately 5 ml with an evaporator. Diethyl ether was then added to precipitate the peptide. This peptide precipitate was collected with a glass filter (G3), washed five times with diethyl ether and upon drying under reduced pressure, 65 mg of peptide H was obtained.

The N-terminal amino group of all amino acids were protected with the Fmoc group and the functional side chains were protected with the following groups before using the amino acids in the reaction:

Arg-Mtr: (4-methoxy-2,3,6-trimethylbenzensulfonyl)
Lys-Boc: (t-butyloxycarbonyl)
Cys-Trt: (trityl)
His-Boc: (t-butyloxycarbonyl)

Approximately 10 mg of the peptide was dissolved in 3.0 ml of a mixed solvent of chloroform-methanol (C/M) 2:1 (V/V). The sample was then purified with a Sephadex LH-60 column (φ2.5 cm×90 cm) that was equilibrated with the C/M mixed solvent 2:1 (V/V) to collect the pure peptide H.

The presence of the peptide in the eluate was monitored at 245 nm (spectrophotometer; Japan Spectroscopic Co.Ltd. Model 870-UV) and with a differential refractometer (Shimadzu corporation Model RID-6A).

FABMS (M+H$^+$); 2663.6 (calculated molecular weight; 2662.5)

EXAMPLE 9

The peptide (peptide I) with [sequence No.13] was prepared in the same manner as in Example 8.

FABMS (M+H$^+$); 2560.4 (calculated molecular weight; 2559.3)

EXAMPLE 10

The peptide (peptide J) with [sequence No.14] was prepared in the same manner as in Example 8.

FABMS (M+H$^+$); 2663.8 (calculated molecular weight; 2662.5)

EXAMPLE 11

The peptide (peptide K) with [sequence No.15] was prepared in the same manner as in Example 2.

FABMS (M+H$^+$); 2663.5 (calculated molecular weight; 2662.5)

EXAMPLE 12

The peptide (peptide L) with [sequence No.16] was prepared in the same manner as in Example 2.

FABMS (M+H$^+$); 2503.6 (calculated molecular weight; 2502.4)

EXAMPLE 13

The peptide (peptide M) with [sequence No.17] was prepared in the same manner as in Example 2.

FABMS (M+H$^+$); 2736.7 (calculated molecular weight; 2735.5)

EXAMPLE 14

The peptide (peptide N) with [sequence No.18] was prepared in the same manner as in Example 2.

FABMS (M+H$^+$); 2640.4 (calculated molecular weight; 2639.4)

EXAMPLE 15

The peptide (peptide O) with [sequence No.19] was prepared in the same manner as in Example 8.

FABMS (M+H$^+$); 2640.3 (calculated molecular weight; 2639.4)

EXAMPLE 16

Fmoc-Pro-Val-His(Trt)-Leu-Lys(Boc)-Arg(Mtr)

The peptide (peptide P) of the title was synthesized by a solid phase method using the Peptide Synthesizer System 9050 (Millipore Corp.).

N-α-9-fluorenylmethylcarbonyl-N-ω-4-methoxy-2,3,6,-trimethylbenzensulfonyl-arginine-O-resin (Fmoc-Arg(Mtr)-O-resin) (0.20 mmol), in which N-α-9-fluorenylmethylcarbonyl-N-ω-4-methoxy-2,3,6,-trimethylbenzensulfonyl-arginine (Fmoc-Arg(Mtr)) is bonded to 2-methoxy-4-alkoxybenzylalcohol-resin (Sasrin resin, trade name of Bachem Co.,Ltd.), was used as the starting resin and amino acids were sequentially added in the N-terminal direction on the resin surface according to the synthesis protocol of Peptide Synthesizer System 9050 to synthesize a peptide-O-resin with the N-terminal and the functional groups fully protected.

The fully-protected peptide-O-resin was then washed five times with methanol and dried under reduced pressure. A TFA-dichloromethane solution (1:99, V/V) was then added to the dried peptide-O-resin (330 mg) while stirring and cooling with ice. The mixture was then stirred while cooling under ice for 30 minutes and then stirred for 90 minutes at room temperature to remove the peptide from the resin with the protective groups still attached to the peptide. The mixture was then filtered with a glass filter (G3) and the filtrate was concentrated under reduced pressure to approximately 5 ml using an evaporator. Diethyl ether was then added to precipitate the peptide. This peptide precipitate was collected with a glass filter (G3), then washed five times with diethyl ether and dried under reduced pressure. 180 mg of peptide P was thus obtained.

The N-terminal amino group of all amino acids were protected with the Fmoc group and the functional side chains were protected with the following groups before using the amino acids in the reaction:

Arg-Mtr: (4-methoxy-2,3,6-trimethylbenzensulfonyl)
Lys-Boc: (t-butyloxycarbonyl)
His-Trt: (trityl)

A TFA-dichloromethane (1:99, V/V) solution was then added to the crude peptide to prepare a 10 mg/ml sample solution which was purified by HPLC using an Asahipak GS-510 (φ21.5×500 mm) column (trade name; Asahi Chemical Industry Co.Ltd.) to collect pure peptide P.

A TFA-dichloromethane (1:99, V/V) solution was used as the eluant and elution was carried out at flow rate of 8.1 ml/min for 120 minutes. The presence of the peptide in the eluate was monitored at 245 nm (spectrophotometer; Japan Spectroscopic Co.Ltd. Model 870-UV) and with a differential refractometer (Shimadzu corporation Model RID-6A).

FABMS (M+H$^+$); 1405.0 (calculated molecular weight; 1403.8)

EXAMPLE 17

H-Nle-(Nle)14-Nle-O-resin was synthesized with a solid phase multi-peptide synthesis system in accordance with Example 8.

Next, after adding DMF to the synthesized H-Nle-(Nle)14-Nle-O-resin, peptide P was added instead of Fmoc-Arg(Mtr). N-hydroxybenzotriazole and N,N'-diisopropylcarbodiimide were added and the mixture was then shaken for 8 hours. This condensation reaction was carried out two times. The condensation reaction was checked with the ninhydrin method kaiser test.

Thereafter, in accordance with the method of Example 8, the protective groups of the functional groups were eliminated and the peptide was removed from the resin and purified by HPLC to prepare the peptide (peptide I) with [sequence No. 13].

FABMS (M+H$^+$); 2560.2 (calculated molecular weight; 2559.3)

EXAMPLE 18

A peptide (peptide Q) with the thiol groups of peptide D being of an acetoamidomethylated (ACM) form was prepared in the same manner as in Example 4 except for that Fmoc-Cys(ACM) was used instead of Fmoc-Cys(Trt).

FABMS (M+H$^+$); 2734.7 (calculated molecular weight; 2733.6)

24, 48 and 72 hours and the hydrolysis products were analyzed with a Shimadzu Automatic Amino Acid Analysis System (LC-9A) after removing the acid. The Trp of peptide M was alkali hydrolyzed with 4.2N aqueous sodium hydroxide for 16, 24 and 32 hours and then neutralized with HCl and then analyzed with the Amino Acid Analysis System. The amino acid composition, computed from the amino acid values that indicated higher recoveries among the hydrolyses of 1 to 72 hours, indicated values that substantially matched the values calculated from the chemical formulae.

The results are shown in Table 1.

TABLE 1

Amino acid compositions of the synthetic peptides of the invention

| Amino acid | A | B | C | D | E | F | G | H | I | J | K | L | M | N | O | S | T |
|---|---|---|---|---|---|---|---|---|---|---|---|---|---|---|---|---|---|
| Lys | 1.1 | 0.9 | 1.0 | 0.8 | 0.9 | 1.0 | 0.7 | 0.7 | 1.1 | 1.1 | 0.9 | 1.2 | 0.9 | 1.2 | 0.9 | 1.3 | 0.9 |
| Arg | 1.0 | 1.1 | 0.9 | 0.8 | 0.9 | 0.7 | 0.8 | 0.9 | 1.0 | 0.9 | 1.0 | 1.0 | 1.1 | 1.1 | 1.2 | 1.0 | 1.2 |
| His | 1.0 | 1.0 | 1.0 | 1.0 | 1.0 | 1.0 | 1.0 | 1.0 | 1.0 | 1.0 | 1.0 | 1.0 | 1.0 | — | — | 1.0 | 1.0 |
| Gly | 3.2 | 1.2 | — | — | — | — | 1.1 | — | — | — | — | — | — | — | — | 1.1 | 1.0 |
| Ser | — | — | — | — | — | 0.8 | — | — | — | — | — | — | — | — | — | — | — |
| Cys | 1.9 | 1.3 | 1.0 | 0.9 | 1.1 | — | 0.8 | 0.7 | — | 0.7 | 0.9 | 0.8 | 0.6 | 0.7 | 0.8 | 0.6 | 0.8 |
| Ala | 0.9 | 1.0 | — | — | — | — | 0.8 | — | — | — | — | — | — | — | — | 1.1 | 0.9 |
| Val | 0.9 | 1.0 | 0.8 | 0.9 | 0.8 | 1.2 | 0.8 | 0.8 | 0.9 | 1.1 | 1.0 | 3.9 | 0.9 | 1.0 | 0.9 | 16.5 | 0.9 |
| Leu | 19.5 | 18.7 | 20.5 | 16.8 | 13.1 | 16.9 | 3.1 | 1.1 | 0.9 | 8.9 | 13.6 | 11.8 | 15.7 | 16.8 | — | 2.8 | 2.7 |
| Ile | 1.0 | — | — | — | — | — | — | — | — | — | 2.9 | — | — | — | 0.9 | — | 15.6 |
| Met | 1.1 | — | — | — | — | — | — | — | — | — | — | — | — | — | — | — | — |
| Pro | 2.3 | 1.2 | 0.9 | 0.7 | 0.8 | 0.8 | 0.7 | 0.9 | 0.8 | 0.9 | 1.1 | 0.8 | 1.0 | 1.2 | 1.0 | 1.0 | 1.0 |
| Phe | 0.9 | — | — | — | — | — | — | — | — | — | — | — | — | — | — | — | — |
| Nle | — | — | — | — | — | — | 15.7 | 15.9 | 16.1 | 7.9 | — | — | — | — | 15.8 | — | — |
| Nva | — | — | — | — | — | — | — | — | — | — | — | 2.1 | — | — | — | — | — |
| Trp | — | — | — | — | — | — | — | — | — | — | — | — | 0.9 | — | — | — | — |
| Asx | — | — | — | — | — | — | — | — | — | — | — | — | — | 1.0 | 1.0 | — | — |

(The values are for the case where the His content is set to 1.0 exept for peptides N and O for which the values are for the case where the Asx is set to 1.0.)

EXAMPLE 19

Peptide R was prepared by esterifying the thiol groups of peptide E with palmitic acid according the method by Sarin, Virender and Kumar (EP 0 458 167A1).

FABMS (M+H$^+$); 2448.5 (calculated molecular weight; 2448.3)

Comparison Example 1

The peptide (peptide S) with [sequence No.20] was prepared in the same manner as in Example 2.

FABMS (M+H$^+$); 2793.8 (calculated molecular weight; 2792.6)

Comparison Example 2

The peptide (peptide T) with [sequence No.21] was prepared in the same manner as in Example 2.

FABMS (M+H$^+$); 3018.3 (calculated molecular weight; 3016.9)

Amino acid composition analysis of the synthetic peptides of the invention

The synthetic peptides of the invention were acid hydrolyzed with a 12N HCl-TFA solution [2:1 (V/V)] containing 5% (w/v) phenol under vacuum at 150° C. for 1, 2, 4, 6, 12, (2) The production of surfactants of the invention The surfactants of the invention were prepared by mixing the peptides of the invention with the three lipid components of chlorine phosphoglyceride, acidic phospholipid and fatty acid analogue.

EXAMPLE 20

Sterilized quantities of 1,2-dipalmitoylglycero-(3)-phosphocholine (1350 mg), 1,2-diacyl-sn-glycero-(3)-phospho-sn-glycerol (with the acyl group having 14–24 carbons; made by Sigma Chemical Co.,Ltd.)(450 mg) and myrisitic acid (200 mg) were dissolved at room temperature in a chloroform-methanol mixture [2:1 (V/V)](1000 ml) and 25 mg of peptide A was dissolved in TFA (1.0 ml). These solutions were mixed together and then dried and solidified under reduced pressure. The residual obtained was suspended in a water-ethanol mixture [9:1 (V/V)](100 ml) for 15 minutes at 40° C. Upon freezing this suspension at –50° C. and then drying for 36 hours at a vacuum of 85–100 $\mu$Hg, the surfactant (2070 mg) was obtained as a white powder.

There were no detectable quantities of ethanol in this powder and the contents of each of the components with respect to the total weight of the surfactant were 65.2% (W/W) for 1,2-dipalmitoylglycero-(3)-phosphocholine, 21.7% (W/W) for 1,2-diacyl-sn-glycero-(3)-phospho-sn-glycerol, 9.7% (W/W) for myrisitic acid, 1.2% (W/W) for peptide A and 2.2% (W/W) for water.

EXAMPLE 21

The compounds 1,2-dipalmitoylglycero-(3)-phosphocholine (300.0 mg), 1,2-diacyl-sn-glycero-(3)-phospho-sn-glycerol (with the acyl group having 14–24 carbon atoms; made by Sigma Chemical Co.,Ltd.)(100.0 mg) and palmitic acid (40.0 mg) were dissolved in a chloroform-methanol mixture [2:1 (V/V)](300 ml) and 10.0 mg of peptide B was dissolved in a chloroform-methanol mixture [2:1 (V/V)](2.0 ml). These solutions were mixed together and then dried and solidified under reduced pressure. Suspension of the residual resulted in a water-ethanol mixture [9:1 (V/V)](100 ml) was performed for 20 minutes at 45° C. Upon freezing this suspension at −60° C. and drying for 40 hours at a vacuum of 60–110 μHg, 459.1 mg of a white, powdery surfactant was obtained.

There were no detectable quantities of ethanol in this powder and the contents of each of the components with respect to the total weight of the surfactant were 65.3% (W/W) for 1,2-dipalmitoylglycero-(3)-phosphocholine, 21.8% (W/W) for 1,2-diacyl-sn-glycero-(3)-phospho-sn-glycerol, 8.7% (W/W) for palmitic acid, 2.2% (W/W) for peptide B and 2.0% (W/W) for water.

EXAMPLE 22

1,2-dipalmitoylglycero-(3)-phosphocholine (280.0 mg), 1,2-dilauroyl-sn-glycero-(3)-phospho-sn-glycerol (120.0 mg) and palmitic acid (27.0 mg) were dissolved in a chloroform-methanol mixture [2:1 (V/V)](150 ml) and 2.8 mg of peptide C was dissolved in a chloroform-methanol mixture [1:2 (V/V)](0.5 ml). These solutions were mixed together and then dried and solidified under reduced pressure. Suspension of the residual obtained a water-ethanol mixture [8:2 (V/V)](100 ml) was performed for 45 minutes at 40° C. Upon freezing this suspension at −65° C. and drying for 36 hours at a vacuum of 50–80 μHg, 437.6 mg of a white surfactant powder was obtained.

There were no detectable quantities of ethanol in this powder and the contents of each of the components with respect to the total weight of the surfactant were 64.0% (W/W) for 1,2-dipalmitoylglycero-(3)-phosphocholine, 27.4% (W/W) for 1,2-dilauroyl-sn-glycero-(3)-phospho-sn-glycerol, 6.2% (W/W) for palmitic acid, 0.6% (W/W) for peptide C and 1.8% (W/W) for water.

EXAMPLE 23

Besides using peptide D instead of peptide B and using 1-palmitoyl-2-oleoyl-sn-glycero-(3)-phospho-sn-glycerol instead of 1,2-diacyl-sn-glycero-(3)-phospho-sn-glycerol (with the acyl group having 14–24 carbon atoms; made by Sigma Chemical Co.,Ltd.), the same operations as those in Example 21 were performed to produce 451.9 mg of a white surfactant powder.

There were no detectable quantities of ethanol in this powder and the contents of each of the components with respect to the total weight of the surfactant were 66.4% (W/W) for 1,2-dipalmitoylglycero-(3)-phosphocholine, 22.1% (W/W) for 1-palmitoyl-2-oleoyl-sn-glycero-(3)-phospho-sn-glycerol, 8.9% (W/W) for palmitic acid, 2.2% (W/W) for peptide D and 0.4% (W/W) for water.

EXAMPLE 24

1,2-dipalmitoylglycero-(3)-phosphocholine (320.0 mg), 1,2-dimyristoyl-sn-glycero-(3)-phospho-sn-glycerol (80.0 mg) and palmitic acid (60.0 mg) were dissolved in a chloroform-methanol mixture [1:1 (V/V)](200 ml) and peptide E (14.0 mg) was dissolved in TFA(0.3 ml). These solutions were mixed together and then dried and solidified under reduced pressure. Suspension of the residual obtained a water-ethanol mixture [10:1 (V/V)](50 ml) was performed for 60 minutes at 45° C. Upon freezing this suspension at −45° C. and drying for 24 hours at a vacuum of 50–110 μHg, 479.2 mg of a white surfactant powder was obtained.

There were no detectable quantities of ethanol in this powder and the contents of each of the components with respect to the total weight of the surfactant were 66.8% (W/W) for 1,2-dipalmitoylglycero-(3)-phosphocholine, 16.7% (W/W) for 1,2-dimyristoyl-sn-glycero-(3)-phospho-sn-glycerol, 12.5% (W/W) for palmitic acid, 2.9% (W/W) for peptide E and 1.1% (W/W) for water.

EXAMPLE 25

Besides using peptide F (22.0 mg) instead of peptide B (10.0 mg) and using 1,2-distearoyl-sn-glycero-(3)-phospho-sn-glycerol instead of 1,2-diacyl-sn-glycero-(3)-phospho-sn-glycerol (with the acyl group having 14–24 carbon atoms; made by Sigma Chemical Co., Ltd.), the same operations as those in Example 21 were performed to produce 463.9 mg of a white surfactant powder.

There were no detectable quantities of ethanol in this powder and the contents of each of the components with respect to the total weight of the surfactant were 64.7% (W/W) for 1,2-dipalmitoylglycero-(3)-phosphocholine, 21.6% (W/W) for 1,2-distearoyl-sn-glycero-(3)-phospho-sn-glycerol, 8.6% (W/W) for palmitic acid, 4.7% (W/W) for peptide F and 0.4% (W/W) for water.

EXAMPLE 26

Besides using peptide G instead of peptide B, the same operations as those in Example 21 were performed to produce 454.1 mg of a white surfactant powder.

There were no detectable quantities of ethanol in this powder and the contents of each of the components with respect to the total weight of the surfactant were 66.1% (W/W) for 1,2-dipalmitoylglycero-(3)-phosphocholine, 22.0% (W/W) for 1,2-acyl-sn-glycero-(3)-phospho-sn-glycerol (with the acyl group having 14–24 carbon atoms; made by Sigma Chemical Co., Ltd.), 8.8% (W/W) for palmitic acid, 2.2% (W/W) for peptide G and 0.9% (W/W) for water.

EXAMPLE 27

The compound 1,2-dipalmitoylglycero-(3)-phosphocholine (210 mg), 1,2-diacyl-sn-glycero-(3)-phospho-sn-glycerol (with the acyl group having 14–24 carbon atoms; made by Sigma Chemical Co., Ltd.)(90.0 mg) and stearic acid (33.0 mg) were dissolved in a chloroform-methanol mixture [3:1 (V/V)](100 ml) and peptide H (1.9 mg) was dissolved in methanol(0.5 ml). These solutions were mixed together and then dried and solidified under reduced pressure. Suspension of the residual obtained a water-ethanol mixture [9:1 (V/V)](90 ml) was performed for 15 minutes at 50° C. Upon freezing this suspension at −55° C. and drying for 28 hours at a vacuum of 100–120 μHg, 340.2 mg of a white surfactant powder was obtained.

There were no detectable quantities of ethanol in this powder and the contents of each of the components with respect to the total weight of the surfactant were 61.7% (W/W) for 1,2-dipalmitoylglycero-(3)-phosphocholine, 26.5% (W/W) for 1,2-diacyl-sn-glycero-(3)-phospho-sn-glycerol, 9.7% (W/W) for stearic acid, 0.5% (W/W) for peptide H and 1.6% (W/W) for water.

EXAMPLE 28

The compounds 1,2-dipalmitoylglycero-(3)-phosphocholine (210.0 mg), 1-palmitoyl-2-oleoyl-sn-glycero-(3)-phospho-L-serine (90.0 mg) and palmitic acid (33.0 mg) were dissolved in a chloroform-methanol mixture [4:1 (V/V)](100 ml) and peptide I (11.0 mg) was dissolved in TFA (0.5 ml). These solutions were mixed together and then dried and solidified under reduced pressure. Suspension of the residual obtained a water-ethanol mixture [9:1 (V/V)](110 ml) was performed for 25 minutes at 45° C. Upon freezing this suspension at −55° C. and drying for 28 hours at a vacuum of 100–120 $\mu$Hg, 348.7 mg of a white surfactant powder was obtained.

There were no detectable quantities of ethanol in this powder and the contents of each of the components with respect to the total weight of the surfactant were 60.2% (W/W) for 1,2-dipalmitoylglycero-(3)-phosphocholine, 25.8% (W/W) for 1-palmitoyl-2-oleoyl-sn-glycero-(3)-phospho-L-serine, 9.5% (W/W) for palmitic acid, 3.2% (W/W) for peptide I and 1.3% (W/W) for water.

EXAMPLE 29

Besides using peptide J instead of peptide B, the same operations as those in Example 21 were performed to produce 459.3 mg of a white surfactant powder.

EXAMPLE 30

Besides using peptide K instead of peptide B, the same operations as those in Example 21 were performed to produce 452.5 mg of a white surfactant powder.

EXAMPLE 31

Besides using peptide L instead of peptide B, the same operations as those in Example 21 were performed to produce 456.6 mg of a white surfactant powder.

EXAMPLE 32

Besides using peptide M instead of peptide B, the same operations as those in Example 21 were performed to produce 453.9 mg of a white surfactant powder.

EXAMPLE 33

Besides using peptide N instead of peptide B, the same operations as those in Example 21 were performed to produce 452.5 mg of a white surfactant powder.

EXAMPLE 34

Besides using peptide O instead of peptide B, the same operations as those in Example 21 were performed to produce 458.1 mg of a white surfactant powder.

EXAMPLE 35

The compound 1,2-dipalmitoylglycero-(3)-phosphocholine (30.0 mg), 1,2-diacyl-sn-glycero-(3)-phospho-sn-glycerol (with the acyl group having 14–24 carbon atoms; made by Sigma Chemical Co., Ltd.)(10.0 mg) and palmitic acid (4.0 mg) were dissolved in a chloroform-methanol mixture [2:1 (V/V)](30 ml) and 1.0 mg of peptide Q was dissolved in a chloroform-methanol mixture [2:1 (V/V)](2.0 ml). These solutions were mixed together and then dried and solidified under reduced pressure. Suspension of the residual obtained a water-ethanol mixture [9:1 (V/V)](10 ml) was performed for 20 minutes at 45° C. Upon freezing this suspension at −60° C. and drying for 36 hours at a vacuum of 60–120 $\mu$Hg, 45.4 mg of a white surfactant powder was obtained.

There were no detectable quantities of ethanol in this powder and the contents of each of the components with respect to the total weight of the surfactant were 66.1% (W/W) for 1,2-dipalmitoylglycero-(3)-phosphocholine, 22.0% (W/W) for 1,2-diacyl-sn-glycero-(3)-phospho-sn-glycerol, 8.8% (W/W) for palmitic acid, 2.2% (W/W) for peptide Q and 0.9% (W/W) for water.

EXAMPLE 36

Besides using peptide R instead of peptide Q, the same operations as those in Example 35 were performed to produce 45.7 mg of a white surfactant powder.

Comparison Example 3

Besides using a solution of peptide S (10.0 mg) in TFA (0.3 ml) instead of the solution of peptide B (10.0 mg) in a chloroform-methanol mixture [2:1 (V/V)](2.0 ml), the same operations as those in Example 21 were performed to produce 455.2 mg of a white surfactant powder.

There were no detectable quantities of ethanol in this powder and the contents of each of the components with respect to the total weight of the surfactant were 65.9% (W/W) for 1,2-dipalmitoylglycero-(3)-phosphocholine, 22.0% (W/W) for 1,2-acyl-sn-glycero-(3)-phospho-sn-glycerol (with the acyl group having 14–24 carbon atoms; made by Sigma Chemical Co., Ltd.), 8.8% (W/W) for palmitic acid, 2.2% (W/W) for peptide S and 1.1% (W/W) for water.

Comparison Example 4

Besides using a solution of peptide T (10.0 mg) in TFA (0.3 ml) instead of the solution of peptide B (10.0 mg) in a chloroform-methanol mixture [2:1 (V/V)](2.0 ml), the same operations as those in Example 21 were performed to produce 456.0 mg of a white surfactant powder.

There were no detectable quantities of ethanol in this powder and the contents of each of the components with respect to the total weight of the surfactant were 65.8% (W/W) for 1,2-dipalmitoylglycero-(3)-phosphocholine, 21.9% (W/W) for 1,2-acyl-sn-glycero-(3)-phospho-sn-glycerol (with the acyl group having 14–24 carbon atoms; made by Sigma Chemical Co., Ltd.), 8.8% (W/W) for palmitic acid, 2.2% (W/W) for peptide T and 1.3% (W/W) for water.

Table 2 shows the results of the tests on the surface activity and alveolar space volume-maintaining effects of the surfactants by the invention.

Potential Applications in the Industry

As described above, the novel synthetic polypeptides of the invention are easy to isolate and purify, can be made by methods allowing bulk production, have high solubilities in general solvents and indicate better uniform suspensibility and equivalently powerful surface activities in comparison to conventional compositions.

The invention can therefore be used as therapeutic agents for respiratory distress syndrome which is a disease that produces severe respiratory disorders.

TABLE 2

Surface activities and alveolar volume-maintaining effect of the surfactants by the invention.

|  | Surface Activity | | | | | Alveolar volume-maintaining effects |
|---|---|---|---|---|---|---|
|  | Surface tension | Spreadability over a gas-liquid interface | | Absorbability to a gas-liquid interface | | |
|  | lowering effect | Equilib-ration time | Equilibrium surface tension | Equilib-ration time | Equilibrium surface tension | Lung volume |
|  | Max dyne/cm | Min dyne/cm | sec | dyne/cm | sec | dyne/cm | (at 5 cm H$_2$O ml/kg) |
| Example 20 | 29.0 | 0.2 | 30 | 27.5 | 65 | 30.3 | 48 |
| Example 21 | 24.7 | 0.5 | 30 | 26.7 | 30 | 29.2 | 55 |
| Example 22 | 32.6 | 4.3 | 60 | 33.1 | 90 | 34.8 | 41 |
| Example 23 | 26.8 | 2.5 | 40 | 28.5 | 50 | 32.3 | 51 |
| Example 24 | 33.1 | 7.3 | 60 | 33.5 | 100 | 34.6 | 39 |
| Example 25 | 33.7 | 7.4 | 60 | 32.8 | 100 | 34.2 | 39 |
| Example 26 | 27.2 | 1.1 | 60 | 28.3 | 40 | 29.9 | 49 |
| Example 27 | 27.2 | 8.7 | 60 | 27.5 | 50 | 28.3 | 46 |
| Example 28 | 34.1 | 3.9 | 60 | 34.3 | 95 | 36.8 | 40 |
| Example 29 | 28.0 | 0.8 | 30 | 27.6 | 30 | 29.9 | 53 |
| Example 30 | 31.5 | 1.6 | 50 | 28.0 | 80 | 32.1 | 47 |
| Example 31 | 34.2 | 1.2 | 60 | 33.1 | 100 | 34.5 | 40 |
| Example 32 | 33.7 | 3.0 | 30 | 31.6 | 60 | 33.9 | 44 |
| Example 33 | 28.7 | 3.2 | 30 | 26.9 | 50 | 30.2 | 51 |
| Example 34 | 30.8 | 2.1 | 50 | 29.8 | 70 | 31.9 | 49 |
| Example 35 | 30.1 | 2.5 | 40 | 30.4 | 50 | 31.7 | 49 |
| Example 36 | 33.4 | 3.9 | 60 | 31.3 | 90 | 32.9 | 45 |
| Comparison Example 3 | 40.1 | 10.3 | 90 | 37.2 | 180 | 41.5 | 28 |
| Comparison Example 4 | 39.0 | 2.5 | 95 | 36.4 | 150 | 39.7 | 29 |

We claim:

1. A peptide having the following sequence:

Xaa-Pro-Val-Xbb-Xcc-Lys-Arg-W wherein Xaa is either not present or, if present, represents Cys or Ser, wherein an N-terminus of the sequence optionally further comprises an amino acid or amino acids selected from the group consisting of Cys, Ser, and a combination of Cys, or Ser and the sequence Phe-Gly-Ile-Pro; Xbb represents His or Asn; Xcc represents Leu or Ile; and W represents a sequence comprising 12 to 20 molecules of Leu and/or Nle.

2. A peptide according to claim 1, wherein the hydrophobic peptide part contains 1 to 5 molecules selected from the group consisting of Ile, Val, Nva and Trp.

3. A peptide according to claim 1, having a sequence selected from the group consisting of the sequence Nos. 5–19, an S-acetoamidomethylated form of the peptide of sequence No. 8, and an S-palmitoylated form of the peptide of sequence No. 9.

4. A peptide according to claim 1, having the sequence of Sequence No. 5.

5. A peptide according to claim 1, having the sequence of Sequence No. 6.

6. A peptide according to claim 1, having the sequence of Sequence No. 7.

7. A peptide according to claim 1, having the sequence of Sequence No. 8.

8. A peptide according to claim 1, having the sequence of Sequence No. 9.

9. A peptide according to claim 1, having the sequence of Sequence No. 10.

10. A peptide according to claim 1, having the sequence of Sequence No. 11.

11. A peptide according to claim 1, having the sequence of Sequence No. 12.

12. A peptide according to claim 1, having the sequence of Sequence No. 13.

13. A peptide according to claim 1, having the sequence of Sequence No. 14.

14. A peptide according to claim 1, having the sequence of Sequence No. 15.

15. A peptide according to claim 1, having the sequence of Sequence No. 16.

16. A peptide according to claim 1, having the sequence of Sequence No. 17.

17. A peptide according to claim 1, having the sequence of Sequence No. 18.

18. A peptide according to claim 1, having the sequence of Sequence No. 19.

19. A peptide according to claim 1, wherein Xaa is Cys, acylated by a fatty acid with 14 to 18 carbon atoms.

20. A peptide according to claim 19, wherein the fatty acid is palmitic acid.

21. A peptide according to claim 1, wherein Xaa is acetoamidomethylated Cys.

22. A peptide according to claim 1, wherein Xaa is Ser, acylated by a fatty acid with 14 to 18 carbon atoms.

23. A peptide according to claim 22, wherein the fatty acid is palmitic acid.

24. A peptide according to claim 1, wherein Xaa is acetoamidomethylated Ser.

25. A method of producing a peptide comprising condensing (a) a peptide for synthesis of the following sequence:

Xaa-Pro-Val-Xbb-Xcc-Lys-Arg wherein Xaa is either not present, or, if present, represents Cys or Ser, wherein an N-terminus of the sequence optionally further comprises an amino acid or amino acids selected from the group consisting of Cys, Ser and a combination of Cys or Ser and the sequence Phe-Gly-Ile-Pro; Xbb represents His or Asn; and Xcc represents Leu or Ile; wherein the peptide for synthesis has protected functional groups; and (b) a peptide sequence comprising 12 to 20 molecules of Leu and/or Nle.

26. A pulmonary surfactant, comprising:

(a) a peptide of the following sequence:

Xaa-Pro-Val-Xbb-Xcc-Lys-Arg-W wherein Xaa is not either present, or, if present, represents Cys or Ser, wherein an N-terminus of the sequence optionally further comprises an amino acid or amino acids selected from the group consisting of Cys, Ser and a combination of Cys or Ser and the sequence Phe-Gly-Ile-Pro; Xbb represents His or Asn; and Xcc represents Leu or Ile; and W represents a sequence comprising 12 to 20 molecules of Leu and/or Nle; and (b) a component selected from one or more components of the group consisting of a choline phosphoglyceride, an acid phospholipid, and a fatty acid analogue.

27. A method of treating respiratory distress syndrome, comprising the step of administering to a mammal having respiratory distress syndrome a pulmonary surfactant, comprising:

a peptide of the following sequence:

Xaa-Pro-Val-Xbb-Xcc-Lys-Arg-W wherein Xaa is either not present, or, if present, represents Cys or Ser, wherein an N-terminus of the sequence optionally further comprises an amino acid or amino acids selected from the group consisting of Cys, Ser and a combination of Cys or Ser and the sequence Phe-Gly-Ile-Pro; Xbb represents His or Asn; Xcc represents Leu or Ile; and W represents a sequence comprising 12 to 20 molecules of Leu and/or Nle.

28. A method according to claim 27, wherein said pulmonary surfactant further comprises a component selected from one or more components of the group consisting of a choline phosphoglyceride, an acid phospholipid and a fatty acid analogue.

* * * * *